United States Patent [19]

Cantor

[11] Patent Number: 5,631,134
[45] Date of Patent: May 20, 1997

[54] METHODS OF PREPARING PROBE ARRAY BY HYBRIDATION

[75] Inventor: Charles R. Cantor, Boston, Mass.

[73] Assignee: The Trustees of Boston University, Boston, Mass.

[21] Appl. No.: 462,704

[22] Filed: Jun. 5, 1995

Related U.S. Application Data

[62] Division of Ser. No. 322,526, Oct. 17, 1994, Pat. No. 5,503,980, which is a continuation of Ser. No. 972,012, Nov. 6, 1992, abandoned.

[51] Int. Cl.$^6$ .......................... C07H 21/04; C12P 19/34; C12Q 1/68
[52] U.S. Cl. .......................... 435/6; 435/91.1; 435/91.2; 435/91.52; 536/22.1; 536/24.3; 935/77; 935/78
[58] Field of Search .......................... 435/6, 91.1, 91.2, 435/91.52; 935/77, 78; 536/22.1, 20.3

[56] References Cited

U.S. PATENT DOCUMENTS

| | | | |
|---|---|---|---|
| 4,808,520 | 2/1989 | Pattagupta et al. | 435/6 |
| 5,002,867 | 3/1991 | Macevicz . | |
| 5,068,176 | 11/1991 | Vujg et al. . | |
| 5,073,483 | 12/1991 | Lebacq . | |
| 5,106,727 | 4/1992 | Hartley et al. . | |
| 5,112,734 | 5/1992 | Kramer et al. . | |
| 5,112,736 | 5/1992 | Caldwell et al. . | |
| 5,114,839 | 5/1992 | Blocker . | |
| 5,137,806 | 8/1992 | Lamaistre et al. . | |
| 5,149,625 | 9/1992 | Church et al. . | |
| 5,202,231 | 4/1993 | Drmanac et al. . | |
| 5,219,726 | 6/1993 | Evans . | |

FOREIGN PATENT DOCUMENTS

| | | |
|---|---|---|
| 0392546 | 12/1990 | European Pat. Off. . |
| WO89/10977 | 11/1989 | WIPO . |

OTHER PUBLICATIONS

"Optical Properties of Specific Complexes Between Complementary Oligoribonucleotides", Robert B. Gennis et a., *Biochemistry*, vol. 9, No. 24, 1970.

"DNA Sequencing By Hybridization: 100 Bases Read By a Non–gel–based Method", Zaklina Strezoska, *Proc. Natl. Acad. Sci. USA*, vol. 88, pp. 10089–10093, Nov. 1991.

"Improved Chips for Sequencing by Hybridization", P.A. Pevzner, et al., *Journal of Biomolecular Structure & Dynamics*, vol. 9, Issue No. 2, 1991.

"A Method for DNA Sequencing By Hybridization with Oligonucleotide Matrix", K.R. Khrapko et al., *DNA Sequence—J.DNA Sequencing and Mapping*, vol. 1, pp. 375–388, 1991.

"Sequence–Selective Recogntion of DNA by Strand Displacement with a Thymine–Substituted Polyamide", Peter E. Nelson et al., *Science*, vol. 254, Dec. 1991.

"Parallel Analysis of Oligodeoxyribonucleotide (oligonucleotide) interactions. I Analysis of Factors Influencing Oligonucleotide Duplex Formation", Uwe Maskos, et al. *Nucleic Acids Research*, vol. 20, No. 7, pp. 1675–1678, 1992.

(List continued on next page.)

*Primary Examiner*—Stephanie W. Zitomer
*Assistant Examiner*—Paul B. Tran
*Attorney, Agent, or Firm*—James Remenick; Baker & Botts, L.L.P.

[57] ABSTRACT

This invention is directed to methods for determining a nucleotide sequence of a nucleic acid using positional sequencing by hybridization, and to the creation of nucleic acids probes which may be used with these methods. This invention is also directed to diagnostic aids for analyzing the nucleic acid composition and content of biological samples, including samples derived from medical and agricultural sources.

18 Claims, 8 Drawing Sheets

OTHER PUBLICATIONS

"Analyzing and Comparing Nucleic Acid Sequences by Hybridization to Arrays of Olignucleotides: Evaluation Using Experimental Models", E.M. Southern, *Geonomics*, 13, 1008–1017, 1992.

"Oligonucleotide Hybridization of Glass Supports: A Novel Linker for Oligonucleotide Synthesis and Hybridization Properties of Oligonuclelotides Synthesized in Situ," Uwe Maskos, *Nucleic Acids Research*, vol. 20, No. 7 pp. 1679–1684, 1992.

"Encoded Combinatorial Chemistry", Sydney Brenner, *Proc. Natl. Acad. Sci. USA*, vol. 89, pp. 5381–5383, Jun. 1992.

"Report on the Sequencing by Hybridization Workshop", C.R. Cantor, *Genomics* 13, 1378–1383, 1992.

"I-Turple DNA Sequencing: Computer Analysis", P.A. Pevzner, *Journal of Biomolecular Structure & Dynamics*, vol. 7, Issue No. 1, pp. 063–069, 1989.

"An Oligonucleotide Hybridization Approach To DNA Sequencing", K.R. Khrapko, et al., *Federation of European Biochemical Societies*, vol. 256, No. 1,2, pp. 118–122, Oct. 1989.

"A New Method For Determining The DNA Nucleotide Sequence By Hybridization With Oligonucleotides", Y.P. Lysov, et al., *Plenum Publishing Corporation*, pp. 436–438, 1989.

"Rapid Detection And Sequencing Of Specific In Vitro Amplified DNA Sequences Using Solid Phase Methods", J. Wahlberg, et al., *Mol. Cell. Probes*, 4(4), pp. 285–297, 1990.

"An Algorithm For The DNA Sequence Generation From K-Tuple World Contents Of The Minimal Number Of Random Fragments", R. Drmanac, et al., *Journal of Biomolecular Structure & Dynamics*, vol. 8, Issue No. 5, pp. 1085–1102, 1991.

"Laboratory Methods: Reliable Hybridization Of Oligonucleotides As Short As Six Nuclotides", R. Drmanac, et al., *DNA & Cell Biology*, vol. 9, No. 7, pp. 527–534, 1990.

"Review: Analytical Strategies For The Use Of DNA Probes", J. Matthews, et al., *Analytical Biochemistry*, vol. 169, pp. 1–25, Feb. 1988.

Hames et al., "Nucleic Acid Hybridization—A Practical Approach", pp. 17–45, 1985, IRL Press, Oxford–Washington D.C.

Matthews et al., Anal. Biochemistry 169:1–25, 1988.

Stratagene Cloning Systems, 1992 Product Catalog, p. 106.

EXTENSION WILL FAIL WITH pppAp, pppGp, AND pppCp

ARRAY WITH ONE DEGENERATE BASE

|  | LABEL INTENSITY | | |
| --- | --- | --- | --- |
| Chain Terminator: | T | G | A |
| SEQUENCE | | | |
| GGAAT | 2A,2G | – | 2G |
| AAGGT | 2A,2G | 2A | – |
| GAAGT | 2A,2G | – | 1G |
| AGGAT | 2A,2G | 1A | – |
| AGAGT | 2A,2G | 1A | – |
| GAGAT | 2A,2G | – | 1G |
| GGGAT | 1A,3G | – | 3G |
| GGAGT | 1A,3G | – | 2G |
| GAGGT | 1A,3G | – | 1G |
| AGGGT | 1A,3G | 1A | – |
| AAAGT | 3A,1G | 3A | – |
| AAGAT | 3A,1G | 2A | – |
| AGAAT | 3A,1G | 1A | – |
| GAAAT | 3A,1G | – | 1G |
| GGGGT | 4A | – | 1T,4G* |
| AAAAT | 4G | 1T,4A* | – |

FIG. 8

TEST SEQUENCES 5 bp overlap, perfect match

```
                              TCG AGA ACC TTG GCT*   5'     SEQ ID NO. 1
       3' CTA CTA GGC TGC GTA GTC                           SEQ ID NO. 2
5' biotin-GAT GAT CCG ACG CAT CAG AGC TC 3'                 SEQ ID NO. 3
```

5 bp overlap, mismatch at 3'end

```
                              TCG AGA ACC TTG GCT*   5'     SEQ ID NO. 1
       3' CTA CTA GGC TGC GTA GTC                           SEQ ID NO. 2
5' biotin-GAT GAT CCG ACG CAT CAG AGC T̲T̲ 3'                 SEQ ID NO. 4
```

6 bp overlap, perfect match

```
                              TCG AGA ACC TTG GCT*   5'     SEQ ID NO. 1
       3' CTA CTA GGC TGC GTA GTC                           SEQ ID NO. 2
5' biotin-GAT GAT CCG ACG CAT CAG AGC TCT 3'                SEQ ID NO. 5
```

6 bp overlap, mismatch 4 bases from 3'end

```
                              TCG AGA ACC TTG GCT*   5'     SEQ ID NO. 1
       3' CTA CTA GGC TGC GTA GTC                           SEQ ID NO. 2
5' biotin-GAT GAT CCG ACG CAT CAG AG̲T̲ TCT 3'                SEQ ID NO. 6
```

FIG. 12B

METHODS OF PREPARING PROBE ARRAY BY HYBRIDATION

REFERENCE TO RELATED APPLICATIONS

This U.S. patent application is a divisional of U.S. patent application, Ser. No. 08/322,526, filed Oct. 17, 1994, which issued as U.S. Pat. No. 5,503,980, on Apr. 2, 1996; which is a continuation of abandoned U.S. patent application Ser. No. 07/972,012, filed Nov. 6, 1992.

BACKGROUND OF THE INVENTION

1. Technical Field

This invention is directed to methods for sequencing nucleic acids by positional hybridization, to procedures combining these methods with more conventional sequencing techniques, to the creation of probes useful for nucleic acid sequencing by positional hybridization, to diagnostic aids useful for screening biological samples for nucleic acid variations, and to methods for using these diagnostic aids.

2. Description of the Prior Art

Since the recognition of nucleic acid as the carrier of the genetic code, a great deal of interest has centered around determining the sequence of that code in the many forms which it is found. Two landmark studies made the process of nucleic acid sequencing, at least with DNA, a common and relatively rapid procedure practiced in most laboratories. The first describes a process whereby terminally labeled DNA molecules are chemically cleaved at single base repetitions (A. M. Maxim and W. Gilbert, Proc. Natl. Acad. Sci. USA 74:560–564, 1977). Each base position in the nucleic acid sequence is then determined from the molecular weights of fragments produced by partial cleavages. Individual reactions were devised to cleave preferentially at guanine, at adenine, at cytosine and thymine, and at cytosine alone. When the products of these four reactions are resolved by molecular weight, using, for example, polyacrylamide gel electrophoresis, DNA sequences can be read from the pattern of fragments on the resolved gel.

The second study describes a procedure whereby DNA is sequenced using a variation of the plus-minus method (F. Sanger et al., Proc. Natl. Acad. Sci. USA 74:5463–67, 1977). This procedure takes advantage of the chain terminating ability of dideoxynucleoside triphosphates (ddNTPs) and the ability of DNA polymerase to incorporate ddNTP with nearly equal fidelity as the natural substrate of DNA polymerase, deoxynucleosides triphosphates (dNTPs). Briefly, a primer, usually an oligonucleotide, and a template DNA are incubated together in the presence of a useful concentration of all four dNTPs plus a limited amount of a single ddNTP. The DNA polymerase occasionally incorporates a dideoxynucleotide which terminates chain extension. Because the dideoxynucleotide has no 3'-hydroxyl, the initiation point for the polymerase enzyme is lost. Polymerization produces a mixture of fragments of varied sizes, all having identical 3' terminal. Fractionation of the mixture by, for example, polyacrylamide gel electrophoresis, produces a pattern which indicates the presence and position of each base in the nucleic acid. Reactions with each of the four ddNTPs allows one of ordinary skill to read an entire nucleic acid sequence from a resolved gel.

Despite their advantages, these procedures are cumbersome and impractical when one wishes to obtain megabases of sequence information. Further, these procedures are, for all practical purposes, limited to sequencing DNA. Although variations have developed, it is still not possible using either process to obtain sequence information directly from any other form of nucleic acid.

A new method of sequencing has been developed which overcomes some of the problems associated with current methodologies wherein sequence information is obtained in multiple discrete packages by hybridization. Instead of having a particular nucleic acid sequenced one base at a time, groups of contiguous bases are determined simultaneously. Advantages in speed, expense and accuracy are clear.

Two general approaches of sequencing by hybridization have been suggested. Their practicality has been demonstrated in pilot studies. In one format, a complete set of $4^n$ nucleotides of length n is immobilized as an ordered array on a solid support and an unknown DNA sequence is hybridized to this array (K. R. Khrapko et al., J. DNA Sequencing and Mapping 1:375–88, 1991). The resulting hybridization pattern provides all n-tuple words in the sequence. This is sufficient to determine short sequences except for simple tandem repeats.

In the second format, an array of immobilized samples is hybridized with one short oligonucleotide at a time (Z. Strezoska et al., Proc. Natl. Acad. Sci. USA 88: 10,089–93, 1991). When repeated $N^4$ times for each oligonucleotide of length n, much of the sequence of all the immobilized samples would be determined. In both approaches, the intrinsic power of the method is that many sequenced regions are determined in parallel. In actual practice the array size is about $10^4$ to $10^5$.

Another powerful aspect of the method is that information obtained is quite redundant, especially as the size of the nucleic acid probe grows. Mathematical simulations have shown that the method is quite resistant to experimental errors and that far fewer than all probes are necessary to determine reliable sequence data (P. A. Pevzner et al., J. Biomol. Struc. & Dyn. 9:399–410, 1991; W. Bains, Genomics 11:295–301, 1991).

In spite of an overall optimistic outlook, there are still a number of potentially severe drawbacks to actual implementation of sequencing by hybridization. First and foremost among these is that $4^n$ rapidly becomes quite a large number if chemical synthesis of all of the oligonucleotide probes is actually contemplated. Various schemes of automating this synthesis and compressing the products into a small scale array, a sequencing chip, have been proposed.

A second drawback is the poor level of discrimination between a correctly hybridized, perfectly matched duplexes, and an end mismatch. In part, these drawbacks have been addressed at least to a small degree by the method of continuous stacking hybridization as reported by a Khrapko et al. (FEBS Lett. 256:118–22, 1989). Continuous stacking hybridization is based upon the observation that when a single stranded oligonucleotide is hybridized adjacent to a double stranded oligonucleotide, the two duplexes are mutually stabilized as if they are positioned side to side due to a stacking contact between them. The stability of the interaction decreases significantly as stacking is disrupted by nucleotide displacement, gap, or terminal mismatch. Internal mismatches are presumably ignorable because their thermodynamic stability is so much less than perfect matches. Although promising, a related problem arise which is distinguishing between weak but correct duplex formation and simple background such as non-specific adsorption of probes to the underlying support matrix.

A third drawback is that detection is monochromatic. Separate sequential positive and negative controls must be run to discriminate between a correct hybridization match, a mis-match, and background.

A fourth drawback is that ambiguities develop in reading sequences longer than a few hundred base pairs on account of sequence recurrences. For example, if a sequence the same length of the probe recurs three times in the target, the sequence position cannot be uniquely determined. The locations of these sequence ambiguities are called branch points.

A fifth drawback is the effect of secondary structures in the target nucleic acid. This could lead to blocks of sequences that are unreadable if the secondary structure is more stable than occurs on the complementary strand.

A final drawback is the possibility that certain probes will have anomalous behavior and for one reason or another, be recalcitrant to hybridization under whatever standard sets of conditions that are ultimately used. A simple example of this is the difficulty in finding matching conditions for probes rich in G/C content. A more complex example could be sequences with a high propensity to form triple helices. The only way to rigorously explore these possibilities is to carry out extensive hybridization studies with all possible oligonucleotides of length n, under the particular format and conditions chosen. This is clearly impractical if many sets of conditions are involved.

SUMMARY OF THE INVENTION

The present invention overcomes the problems and disadvantages associated with current strategies and design and provides a new method for rapidly and accurately determining the nucleotide sequence of a nucleic acid by the herein described methods of positional sequencing by hybridization.

As broadly described herein, this invention is directed to a rapid, accurate, and reproducible method of sequencing a nucleic acid by hybridizing that nucleic acid with a set of nucleic acid probes containing random, but determinable sequences within the single stranded portion adjacent to a double stranded portion wherein the single stranded portion of the set preferably comprises every possible combination of sequences over a predetermined range. Hybridization occurs by complementary recognition of the single stranded portion of a target with the single stranded portion of the probe and is thermodynamically favored by the presence of adjacent double strandedness of the probe.

As broadly described herein, another object of this invention is the integration of molecular biology techniques to the method of positional sequencing by hybridization. This includes such techniques as the use of exonucleases to partially cleave the target nucleic acid prior to hybridization, and the use of polymerase to extend one strand of a target hybridized probe using the target as a template. Polymerization can be of a single nucleotide or of a sequence of nucleotides, as determined by known methods which are easily applied by one of ordinary skill in the art.

As broadly described herein, another object of the present invention is the creation of nucleic acid probes for determining the sequence of an unknown nucleic acid. These probes comprise a double stranded portion, which is preferably constant, a single stranded portion, and a determinable random nucleotide sequence within the single stranded portion which hybridizes to the target. Probes may comprise a complete set of all possible sequences of the random single stranded portion or a set comprising only a portion of all possible combinations.

As broadly described herein, another object of the present invention is the use of nucleic acid probes as diagnostic aids in the analysis of nucleic acids of a biological sample. The invention includes diagnostic aids and methods for using diagnostic aids for the analysis of the relatedness or unrelatedness of one nucleic acid to another. Probes may be created in which an unknown or undetermined nucleotide sequence has been identified as the source of a mutation or genetic variation. Probes created herein may be used to quickly, easily, and accurately identify that mutation or variation without having to perform a single conventional sequencing reaction.

As broadly described herein, another object of this invention is a method for determining the position of a partial sequence within the whole nucleic acid by labeling the nucleic acid of interest at one terminal site with a first detectable label, labeling the nucleic acid of interest at an internal site with a second detectable label, and comparing the relative mounts of the first label with the relative amounts of the second label to determine the position of the partial sequence.

Other objects and advantages of the invention are set forth in part in the description which follows, and in part, will be obvious from this description, or may be learned from the practice of this invention. The accompanying drawings which are incorporated in and constitute a part of this specification, illustrate and, together with this description, serve to explain the principle of the invention.

BRIEF DESCRIPTION OF THE DRAWINGS

FIG. 8 Four color analysis of sequence extensions of the 3' end of a probe using three labeled nucleoside triphosphates and one unlabeled chain terminator.

DESCRIPTION OF THE INVENTION

Figure 1A:
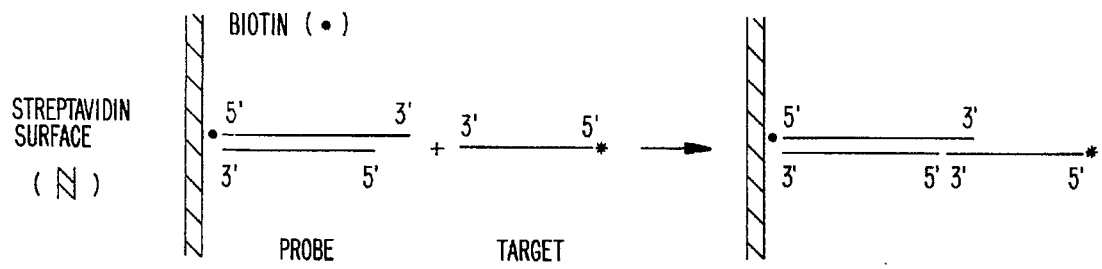
FIG. 1 (A) Shown is the first step of the basic scheme for positional sequencing by hybridization depicting the hybridization of target nucleic acid with probe forming a 5' overhang of the target. (B) Shown is the first step of the alternate scheme for positional sequencing by hybridization depicting the hybridization of target nucleic acid with probe forming a 3' overhang of the probe.

To achieve the objects and in accordance with the purpose of the invention, as embodied and broadly described herein, the present invention comprises methods, probes, diagnostic aids, and methods for using the diagnostic aids to determine sequence information from nucleic acids. Nucleic acids of the present invention include sequences of deoxyribonucleic acid (DNA) or ribonucleic acid (RNA) which may be isolated from natural sources, recombinantly produced, or artificially synthesized. Preferred embodiments of the present invention is probe synthesized using traditional chemical synthesis, using the more rapid polymerase chain reaction (PCR) technology, or using a combination of these two methods.

Nucleic acids of the present invention further include polyamide nucleic acid (PNA) or any sequence of what are commonly referred to as bases joined by a chemical backbone that have the ability to base pair, or hybridize, with a complementary chemical structure. The bases of DNA, RNA, and PNA are purines and pyrimidines linearly linked to a chemical backbone. Common chemical backbone structures are deoxyribose phosphate and ribose phosphate. Recent studies demonstrated that a number of additional structures may also be effective, such as the polyamide backbone of PNA (P. E. Nielsen et al., Sci. 254:1497–1500, 1991).

The purines found in both DNA and RNA are adenine and guanine, but others known to exist are xanthine, hypoxanthine, 2, 1,-diaminopurine, and other more modified bases. The pyrimidines are cytosine, which is common to both DNA and RNA, uracil found predominantly in RNA, and thyrmidine which occurs exclusively in DNA. Some of the more atypical pyrimidines include methylcytosine, hydroxymethylcytosine, methyluracil, hydroxymethyluracil, dihydroxypentyluracil, and other base modifications. These bases interact in a complementary fashion to form basepairs, such as, for example, gunnine with cytosine and adenine with thymidine. However, this invention also encompasses situations in which there is nontraditional base pairing such as Hoogsteen base pairing which has been identified in certain tRNA molecules and postulated to exist in a triple helix.

One embodiment of the present invention is a method for determining a nucleotide sequence by positional hybridization comprising the steps of (a) creating a set of nucleic acid probes wherein each probe has a double stranded portion, a single stranded portion, and a random sequence within the single stranded portion which is determinable, (b) hybridizing a nucleic acid target which is at least partly single stranded to the set of nucleic acid probes, and (c) determining the nucleotide sequence of the target which hybridized to the single strand portion of any probe. The set of nucleic acid probes and the target nucleic acid may comprise DNA, RNA, PNA, or any combination thereof, and may be derived from natural sources, recombinant sources, or be synthetically produced. Each probe of the set of nucleic acid probes has a double stranded portion which is preferably about 10 to 30 nucleotides in length, a single stranded portion which is preferably about 4 to 20 nucleotides in length, and a random sequence within the single stranded portion which is preferably about 4 to 20 nucleotides in length and more preferably about 5 nucleotides in length. A principle advantage of this probe is in its structure. Hybridization of the target nucleic acid is encouraged due to the favorable thermodynamic conditions established by the presence of the adjacent double strandedness of the probe. An entire set of probes contains at least one example of every possible random nucleotide sequence.

By way of example only, if the random portion consisted of a four nucleotide sequence of adenine, guanine, thymine, and cytosine, the total number of possible combinations would be $4^4$ or 256 different nucleic acid probes. If the number of nucleotides in the random sequence was five, the number of different probes within the set would be $4^5$ or 1,024. This becomes a very large number indeed when considering sequences of 20 nucleotides or more.

However, to determine the complete sequence of a nucleic acid target, the set of probes need not contain every possible combination of nucleotides of the random sequence to be encompassed by the method of this invention. This variation of the invention is based on the theory of degenerated probes proposed by S. C. Macevicz (U.S. Pat. No. 5,002,867, and herein specifically incorporated by reference). The probes are divided into four subsets. In each, one of the four bases is used at a defined number of positions and all other bases except that one on the remaining positions. Probes from the first subset contain two elements, A and non-A (A=adenosine). For a nucleic acid sequence of length k, there are $4(2^k-1)$, instead of $4^k$ probes. Where k=8, a set of probes would consist of only 1020 different members instead of the entire set of 65,536. The savings in time and expense would be considerable. In addition, it is also a method of the present invention to utilize probes wherein the random nucleotide sequence contains gapped segments, or positions along the random sequence which will base pair with any nucleotide or at least not interfere with adjacent base pairing.

Hybridization between complementary bases of DNA, RNA, PNA, or combinations of DNA, RNA and PNA, occurs under a wide variety of conditions such as variations in temperature, salt concentration, electrostatic strength, and buffer composition. Examples of these conditions and methods for applying them are described in *Nucleic Acid Hybridization: A Practical Approach* (B. D. Hames and S. J. Higgins, editors, IRL Press, 1985), which is herein specifically incorporated by reference. It is preferred that hybridization takes place between about 0° C. and about 70° C., for periods of from about 5 minutes to hours, depending on the nature of the sequence to be hybridized and its length. It is also preferred that hybridization between nucleic acids be facilitated using certain reagents and chemicals. Preferred examples of these reagents include single stranded binding proteins such as Rec A protein, T4 gene 32 protein, *E. coli* single stranded binding protein, and major or minor nucleic acid groove binding proteins. Preferred examples of other reagents and chemicals include divalent ions, polyvalent ions, and intercalating substances such as ethidium bromide, actinomycin D, psoralen, and angelicin.

The nucleotide sequence of the random portion of each probe is determinable by methods which are well-known in the art. Two methods for determining the sequence of the nucleic acid probe are by chemical cleavage, as disclosed by Maxim and Gilbert (1977), and by chain extension using ddNTPs, as disclosed by Sanger et al. (1977), both of which are herein specifically incorporated by reference. Alternatively, another method for determining the nucleotide sequence of a probe is to individually synthesize each member of a probe set. The entire set would comprise every possible sequence within the random portion or some smaller portion of the set. The method of the present invention could then be conducted with each member of the set. Another procedure would be to synthesize one or more sets of nucleic acid probes simultaneously on a solid support. Preferred examples of a solid support include a plastic, a ceramic, a metal, a resin, a gel, and a membrane. A more preferred embodiment comprises a two-dimensional or three-dimensional matrix, such as a gel, with multiple probe binding sites, such as a hybridization chip as described by Pevzner et al. (J. Biomol. Struc. & Dyn. 9:399–410, 1991), and by Maskos and Southern (Nuc. Acids Res. 20:1679–84, 1992), both of which are herein specifically incorporated by reference.

Hybridization chips can be used to construct very large probe arrays which are subsequently hybridized with a target nucleic acid. Analysis of the hybridization pattern of the chip provides an immediate fingerprint identification of the target nucleotide sequence. Patterns can be manually or computer analyzed, but it is clear that positional sequencing by hybridization lends itself to computer analysis and automation. Algorithms and software have been developed for sequence reconstruction which are applicable to the methods described herein (R. Drmanac et al., J. Biomol. Struc.& Dyn. (in press); P. A. Pevzner, J. Biomol. Struc. & Dyn. 7:63–73, 1989, both of which are herein specifically incorporated by reference).

Another embodiment of the invention comprises target nucleic acid labeled with a detectable label. Label may be incorporated at a 5' terminal site, a 3' terminal site, or at an internal site within the length of the nucleic acid. Preferred detectable labels include a radioisotope, a stable isotope, an enzyme, a fluorescent chemical, a luminescent chemical, a chromatic chemical, a metal, an electric charge, or a spatial structure. There are many procedures whereby one of ordinary skill can incorporate detectable label into a nucleic acid. For example, enzymes used in molecular biology will incorporate radioisotope labeled substrate into nucleic acid. These include polymerases, kinases, and transferases. The labeling isotope is preferably, $^{32}P$, $^{35}S$, $^{14}C$, or $^{125}L$.

Label may be directly or indirectly detected using scintillation fluid or a PhosphorImager, chromatic or fluorescent labeling, or mass spectrometry. Other, more advanced methods of detection include evanescent wave detection of surface plasmon resonance of thin metal film labels such as gold, by, for example, the BIAcore sensor sold by Pharmacia, or other suitable biosensors.

Another embodiment of the present invention comprises a method for determining a nucleotide sequence of a nucleic acid comprising the steps of labeling the nucleic acid with a first detectable label at a terminal site, labeling the nucleic acid with a second detectable label at an internal site, identifying the nucleotide sequences of portions of the nucleic acid, determining the relationship of the nucleotide sequence portions to the nucleic acid by comparing the first detectable label and the second detectable label, and determining the nucleotide sequence of the nucleic acid. Fragments of target nucleic acids labeled both terminally and internally can be distinguished based on the relative amounts of each label within respective fragments. Fragments of a target nucleic acid terminally labeled with a first detectable label will have the same amount of label as fragments which include the labeled terminus. However, theses fragments will have variable amounts of the internal label directly proportional to their size and distance for the terminus. By comparing the relative amount of the first label to the relative amount of the second label in each fragment, one of ordinary skill is able to determine the position of the fragment or the position of the nucleotide sequence of that fragment within the whole nucleic acid.

A further embodiment of the present invention is a method for determining a nucleotide sequence by hybridization comprising the steps of (a) creating a set of nucleic acid probes wherein each probe has a doubled stranded portion, a single stranded portion, and a random sequence within the single stranded portion which is determinable, (b) hybridizing a nucleic acid target which is at least party single stranded to the set, (c) ligating the hybridized target to the probe, and (d) determining the nucleic sequence of the target which is hybridized to the single stranded portion of any probe. This embodiment adds a step wherein the hybridized target is ligated to the probe. Ligation of the target nucleic acid to the complementary probe increases fidelity of hybridization and allows for incorrectly hybridized target to be easily washed from correctly hybridized target (see FIG. 11). Ligation can be accomplished using a eukaryotic derived or a prokaryotic derived ligase. Preferred is T4 DNA or RNA ligase. Methods for use of these and other nucleic acid modifying enzymes are described in *Current Protocols in Molecular Biology* (F. M. Ausubel et al., editors, John Wiley & Sons, 1989), which is herein specifically incorporated by reference.

Another embodiment of the present invention is a method for determining a nucleotide sequence by hybridization which comprises the steps of (a) creating a set of nucleic acid probes wherein each probe has a double stranded portion, a single stranded portion, and a random sequence within the single stranded portion which is determinable, (b) hybridizing a target nucleic acid which is at least partly single stranded to the set of nucleic acid probes, (c) enzymatically extending a strand of the probe using the hybridized target as a template, and (d) determining the nucleotide sequence of the single stranded portion of the target nucleic acid. This embodiment of the invention is similar to the previous embodiment, as broadly described herein, and includes all of the aspects and advantages described therein. An alternative embodiment also includes a step wherein hybridized target is ligated to the probe. Ligation increases the fidelity of the hybridization and allows for a more stringent wash step wherein incorrectly hybridized, unligated target can be removed.

Hybridization produces either a 5' overhang or a 3' overhang of target nucleic acid. Where there is a 5' overhang, a 3- hydroxyl is available on one strand of the probe from which nucleotide addition can be initiated. Preferred enzymes for this process include eukaryotic or prokaryotic polymerases such as T3 or T7 polymerase, Klenow fragment, or Taq polymerase. Each of these enzymes are readily available to those of ordinary skill in the art as are procedures for their use (see *Current Protocols in Molecular Biology*).

Hybridized probes may also be enzymatically extended a predetermined length. For example, reaction condition can be established wherein a single dNTP or ddNTP is utilized as substrate. Only hybridized probes wherein the first nucleotide to be incorporated is complementary to the target sequence will be extended, thus, providing additional hybridization fidelity and additional information regarding the nucleotide sequence of the target. Sanger or Maxim and Gilbert sequencing can be performed which would provide further target sequence data.

Alternatively, hybridization of target to probe can produces 3' extensions of target nucleic acids. Hybridized probes can be extended using nucleoside biphosphate substrates or short sequences which are ligated to the 5' terminus.

Another embodiment of the invention is a method for determining a nucleotide sequence of a target by hybridization comprising the steps of (a) creating a set of nucleic acid probes wherein each probe has a double stranded portion, a single stranded portion, and a random nucleotide sequence within the single stranded portion which is determinable, (b) cleaving a plurality of nucleic acid targets to form fragments of various lengths which are at least partly single stranded, (c) hybridizing the single stranded region of the fragments with the single stranded region of the probes, (d) identifying the nucleotide sequences of the hybridized portions of the fragments, and (e) comparing the identified nucleotide sequences to determine the nucleotide sequence of the target. Another embodiment includes a further step wherein the hybridized fragments are ligated to the probes prior to identifying the nucleotide sequences of the hybridized portions of the fragments.

In these embodiments, target nucleic acid is partially cleaved forming a plurality of nucleic acid fragments of various lengths, a nested set, which is then hybridized to the probe. It is preferred that cleavage occurs by enzymatic, chemical or physical means. Preferred enzymes for partial cleavage are exonuclease III, S1 nuclease, DNase I, Bal 31, mung bean nuclease, P1 nuclease, lambda exonuclease, restriction endonuclease, and RNase I. Preferred means for chemical cleavage are ultraviolet light induced cleavage, ethidium bromide induced cleavage, and cleavage induced with acid or base. Preferred means for mechanical cleavage are shearing through direct agitation such as vortexing or multiple cycles of freeze-thawing. Procedures for enzymatic, chemical or physical cleavage are disclosed in, for example, *Molecular Cloning: A Laboratory Manual* (T. Maniatis et al., editors, Cold Spring Harbor 1989), which is herein specifically incorporated by reference.

Fragmented target nucleic acids will have a distribution of terminal sequences which is sufficiently broad so that the nucleotide sequence of the hybridized fragments will include the entire sequence of the target nucleic acid. A preferred method is wherein the set of nucleic acid probes is fixed to a solid support. A preferred solid support is a plastic, a ceramic, a metal, a resin, a gel, or a membrane, and it is more preferred that the solid support be a two-dimensional or three-dimensional matrix with multiple probe binding sites such as a hybridization chip as described by K. R. Khrapko et al. (1991). It is also preferred wherein the target nucleic acid has a detectable label such as a radioisotope, a stable isotope, an enzyme, a fluorescent chemical, a luminescent chemical, a chromatic chemical, a metal, an electric charge, or a spatial structure.

As an extension of this procedure, it is also possible to use the methods herein described to determine the nucleotide sequence of one or more probes which hybridize with an unknown target sequence. For example, fragmented targets could be terminally or internally labeled, hybridized with a set of nucleic acid probes, and the hybridized sequences of the probes determined. This aspect may be useful when it is cumbersome to determine the sequence of the entire target and only a smaller region of that sequence is of interest.

A further embodiment of the present invention is a method wherein the target nucleic acid has a first detectable label at a terminal site and a second detectable label at an internal site. It is also preferred that the first and second detectable labels are chromatic or fluorescent chemicals or molecules which are detectable by mass spectrometry.

Another embodiment of the invention is a method for creating a nucleic acid probe comprising the steps of (a) synthesizing a plurality of single stranded first nucleic acids and an array of longer single stranded second nucleic acids complementary to the first nucleic acid with a random terminal nucleotide sequence, (b) hybridizing the first nucleic acids to the second nucleic acids to form hybrids having a double stranded portion and a single stranded portion with the random nucleotide sequence within the single stranded portion, (c) hybridizing a single stranded nucleic acid target to the hybrids, (d) ligating the hybridized target to the first nucleic acid of the hybrid, (e) isolating the second nucleic acid, and (f) hybridizing the first nucleic acid of step (a) with the isolated second nucleic acid to form a nucleic acid probe. Probes created in this manner are referred to herein as customized probes.

Preferred customized probe comprises a first nucleic acid which is about 15–25 nucleotides in length and the second nucleic acid is about 20–30 nucleotides in length. It is also preferred that the double stranded portion contain an enzyme recognition site which allows for increased flexibility of use and facilitates cloning, should it at some point become desirable to clone one or more of the probes. It is also preferred if the customized probe is fixed to a solid support, such as, a plastic, a ceramic, a metal, a resin, a gel, or a membrane.

Customized probes, created by the method of this invention, have a wide range of uses. These probes are, first of all, structurally useful for identifying and binding to only those sequences which are homologous to the overhangs. Secondly, the overhangs of these probes possess the nucleotide sequence of interest. No further manipulation is required to carry the sequence of interest to another structure. Therefore, the customized probes greatly lend themselves to use in, for example, diagnostic aids for the genetic screening of a biological sample.

A further embodiment of the present invention is a method for using the customized probe described herein in a diagnostic aid to screen a biological sample. Diagnostic aids and methods for using diagnostic aids would be very useful when sequence information at a particular locus of, for example, DNA is desired. Single nucleotide mutations or more complex nucleic acid fingerprints can be identified and analyzed quickly, efficiently, and easily. Such an approach would be immediately useful for the detection of individual and family genetic variation, of inherited mutations such as those which cause a disease, DNA dependent normal phenotypic variation, DNA dependent somatic variation, and the presence of heterologous nucleic acid sequences. As herein described, these diagnostic aids would be useful in humans, animals, bacteria, fungi and plants.

Diagnostic aids could comprise specific nucleic acid probes fixed to a solid support to which is added the biological sample. Hybridization of target nucleic acids could be determined by adding a detectable label, such as a labeled antibody, which will specifically recognize only hybridized targets or, alternatively, unhybridized target is washed off and labeled target specific antibodies are added. In either case, appearance of label on the solid support indicates the presence of nucleic acid target hybridized to the probe and consequently, within the biological sample.

Customized probes may also prove useful in prophylaxis or therapy by directed a drug, antigen, or other substance to a nucleic acid target with which it will hybridize. The substance to be targeted can be bound to the probe so as not to interfere with possible hybridization. For example, if the probe was targeted to a viral nucleic acid target, an effective antiviral could be bound to the probe which will then be able to specifically carry the antiviral to infected cells. This would be especially useful when the treatment is harmful to normal cells and precise targeting is required for efficacy.

Another embodiment of the present invention is a method for creating a nucleic acid probe comprising the steps of (a) synthesizing a plurality of single stranded first nucleic acids and an array of longer single stranded second nucleic acids complementary to the first nucleic acid with a random terminal nucleotide sequence, (b) hybridizing the first nucleic acids to the second nucleic acids to form hybrids having a double stranded portion and a single stranded portion with the random nucleotide sequence within the single stranded portion, (c) hybridizing a single stranded nucleic acid target to the hybrids, (d) ligating the hybridized target to the first nucleic acid of the hybrid, (e) hybridizing the ligated hybrid with an array of oligonucleotides with random nucleotide sequences, (f) ligating the hybridized oligonucleotide to the second nucleic acid of the ligated hybrid, (g) isolating the second nucleic acid, and (h) hybridizing the first nucleic acid of step (a) with the isolated second nucleic acid to form a nucleic acid probe. Preferred is that the first nucleic acid is about 15–25 nucleotides in length, that the second nucleic acid is about 20–30 nucleotides in length, that the constant portion contain an enzyme recognition site, and that the oligonucleotides are each about 4–20 nucleotides in length. Probes may be fixed to a solid support such as a plastic, ceramic, a metal, a resin, a gel, or a membrane. It is preferred that the solid support be a two-dimensional or three-dimensional matrix with multiple probe binding sites such as a hybridization chip.

Nucleic acid probes created by the method of the present invention are useful in a diagnostic aid to screen a biological sample for genetic variations of nucleic acid sequences therein.

Another embodiment of the present invention is a method for creating a nucleic acid probe comprising the steps of (a) synthesizing a plurality of single stranded first nucleic acids and a set of longer single stranded second nucleic acids complementary to the first nucleic acid with a random terminal nucleotide sequence, (b) hybridizing the first nucleic acids to the second nucleic acids to form hybrids having a double stranded portion and a single stranded portion with the random nucleotide sequence in the single stranded portion, (c) hybridizing a single stranded nucleic acid target to the hybrids, (d) ligating the hybridized target to the first nucleic acid of the hybrid, (e) enzymatically extending the second nucleic acid using the target as a template, (f) isolating the extended second nucleic acid, and (g) hybridizing the first nucleic acid of step (a) with the isolated second nucleic acid to form a nucleic acid probe. It is preferred that the first nucleic acid is about 15–25 nucleotides in length, that the second nucleic acid is about 20–30 nucleotides in length, and that the double stranded portion contain an enzyme recognition site. It is also preferred that the probe be fixed to a solid support, such as a plastic, ceramic, a metal, a resin, a gel, or a membrane. A preferred solid support is a two-dimensional or three-dimensional matrix with multiple probe binding sites, such as a hybridization chip. A further embodiment of the present invention is a diagnostic aid comprising the created nucleic acid probe and a method for using the diagnostic aid to screen a biological sample as herein described.

As an extension of this procedure, it is also possible to use the methods herein described to determine the nucleotide sequence of one or more probes which hybridize with an unknown target sequence. For example, Sanger dideoxynucleotide sequencing techniques could be used when enzymatically extending the second nucleic acid using the target as a template and labeled substrate, entended products could be resolved by polyacrylamide gel electrophoresis, and the hybridized sequences of the probes easily read off the gel. This aspect may be useful when it is cumbersome to determine the sequence of the entire target and only a smaller region of that sequence is of interest.

EXAMPLE 1

Terminal Sequencing by Positional Hybridization

Figure 11:
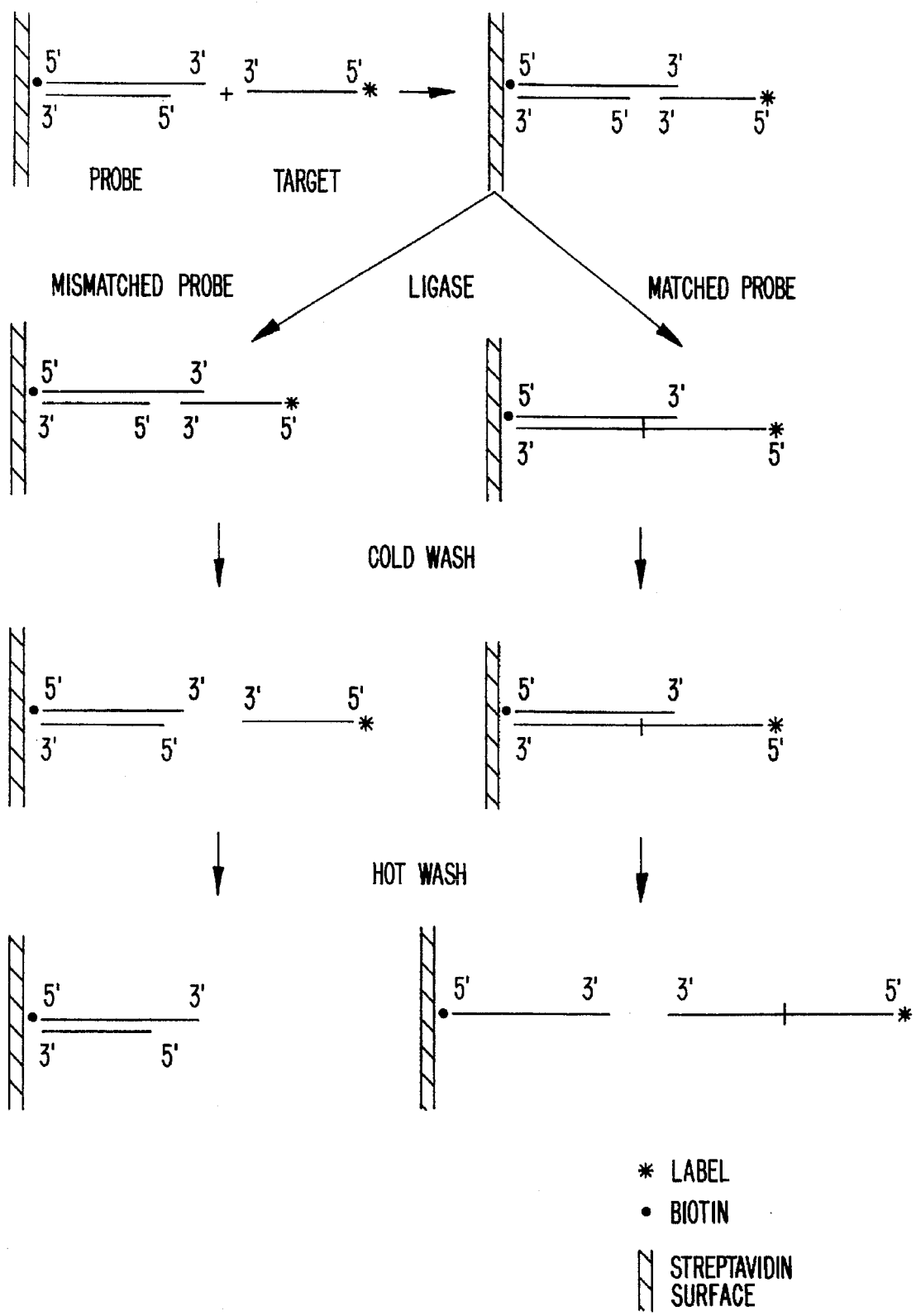
FIG. 11 Graphic representation of the general procedure of positional sequencing by hybridization.

The basic sequencing by hybridization scheme is depicted in FIG. 11. It is different from any other because it uses a duplex oligonucleotide array with 3'-ended single stranded overhangs. The duplex portion of each DNA shown is constant. Only the overhangs vary, and in principle an array of $4^n$ probes is needed to represent all $4^n$ possible overhangs of length n. The advantage of such an array is that it provides enhanced sequence stringency in detecting the 5' terminal nucleotide of the target DNA because of base stacking between the preformed DNA duplex and the newly formed duplex.

One variable is the length of the single stranded overhang. The shorter the overhang, the smaller the array of probes potentially useable. Overhangs of five and six have been successfully employed. The nature of the support surface to which the oligonucleotide is attached, the means of its attachment, and the length of the oligonucleotide duplex are also important variables. Initially one 5' end-biotinylated strand of the probe duplex is attached to a solid surface. The technology is already well developed for the attachment of nucleic acids to solid supports, such as streptavidin-coated magnetic microbeads and membranes such as the thin gel system.

Another variable is the nucleic acid capacity of the immobilized spot of probe. This determines the detection sensitivity required and is also important where unlabeled DNA may be present that could hybridize competitively with the desired labeled DNA product.

As depicted in FIG. 1A, the 3' overhang of the array can detect the 3'-terminal sequence of the target DNA. These will derive from 5'-end labeled restriction fragments of known DNA sequence cut from vectors so that the target for the immobilized probe will either be at the 3' end, just internal to it, or totally internal. In some subsequent examples, it does not matter whether hybridization is absolutely specific for the 3' end.

Figure 1B:
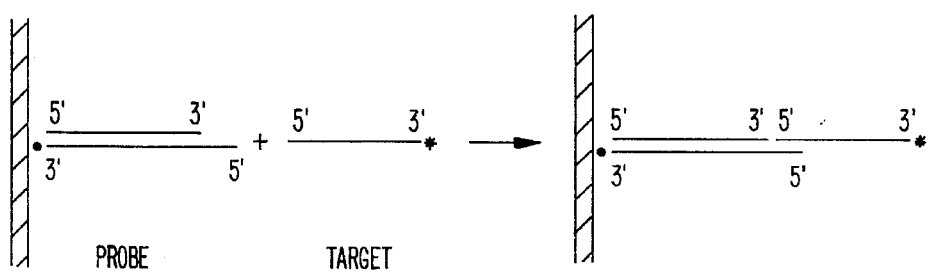

Alternatively, positional sequencing by hybridization of the 5'-end single stranded overhangs would be equally effective (FIG. 1B). This permits reading of the 5' terminal sequence of the target DNA. However, this approach is not as versatile because it does not allow for the use of polymerases to enhance the length and accuracy of the sequence read.

EXAMPLE 2

Preparation of Model Arrays

Figure 2:
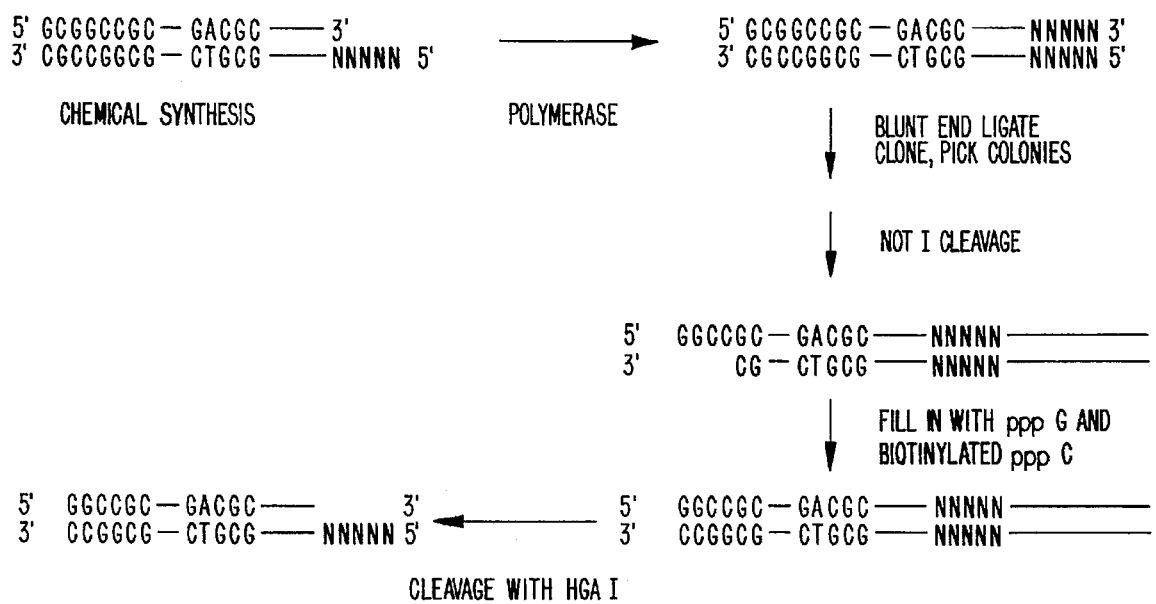
FIG. 2 Preparation of a random probe array.

Following the scheme shown in FIG. 2, in a single synthesis, all 1024 possible single-stranded probes with a constant 18 base stalk followed by a variable 5 base extension can be created. The 18 base extension is designed to contain two restriction enzyme cutting sites. Hga I generates a 5 base, 5' overhang consisting of the variable bases $N_5$. Not I generates a 4 base, 5' overhang at the constant end of the oligonucleotide. The synthetic 23-mer mixture will be hybridized with a complementary 18-mer to form a duplex which can then be enzymatically extended to form all 1024, 23-mer duplexes. These can be cloned by, for example, blunt end ligation, into a plasmid which lacks Not I sites. Colonies containing the cloned 23-base insert can be selected. Each should be a clone of one unique sequence. DNA minipreps can be cut at the constant end of the stalk, filled in with biotinylated pyrimidines, then cut at the variable, end of the stalk, to generate the 5 base 5' overhang. The resulting nucleic acid can be fractionated by Qiagen columns (nucleic acid purification columns) to discard the high molecular weight material, and the nucleic acid probe will then be attached to a streptavidin-coated surface. This procedure could easily be automated in a Beckman Biomec or equivalent chemical robot to produce many identical arrays of probes.

The initial array containing about a thousand probes. The particular sequence at any location in the array will not be known. However, the array can be used for statistical evaluation of the signal to noise ratio and the sequence discrimination for different target molecules under different hybridization conditions. Hybridization with known nucleic acid sequences allows for the identification of particular elements of the array. A sufficient set of hybridizations would train the array for any subsequent sequencing task. Arrays are partially characterized until they have the desired properties. For example, the length of the oligonucleotide duplex, the mode of its attachment to a surface, and the hybridization conditions used, can all be varied, using the initial set of cloned DNA probes. Once the sort of array that works best is determined, a complete and fully characterized array can then be constructed by ordinary chemical synthesis.

EXAMPLE 3

DNA Ligation to Oligonucleotide Arrays

Figure 3A:
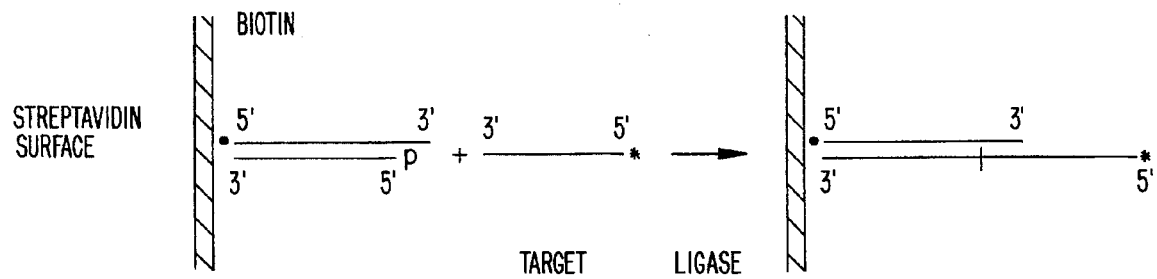
FIG. 3 Graphic representation of the ligation step of positional sequencing by hybridization wherein hybridization of the target nucleic acid produces (A) a 5' overhang or (B) a 3' overhang.
Figure 3B:
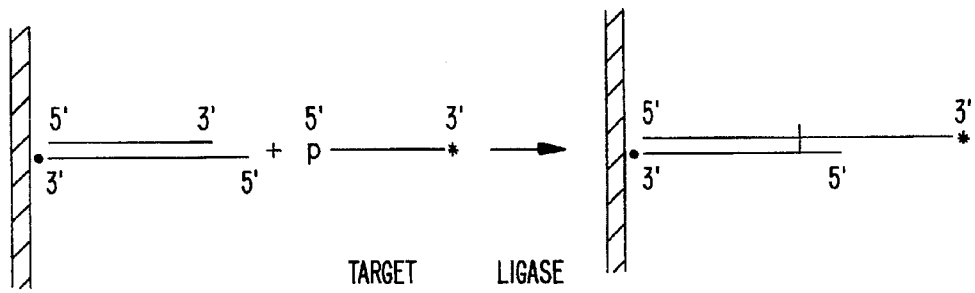

Following the schemes shown in FIGS. 3A and 3B, E. coli and T4 DNA ligases can be used to covalently attach hybridized target nucleic acid to the correct immobilized oligonucleotide probe. This is a highly accurate and efficient process. Because ligase absolutely requires a correctly base paired 3' terminus, ligase will read only the 3'-terminal sequence of the target nucleic acid. After ligation, the resulting duplex will be 23 base pairs long and it will be possible to remove unhybridized, unligated target nucleic acid using fairly stringent washing conditions. Appropriately chosen positive and negative controls demonstrate the power of this scheme, such as arrays which are lacking a 5' terminal phosphate adjacent to the 3' overhang since these probes will not ligate to the target nucleic acid.

There are a number of advantages to a ligation step. Physical specificity is supplanted by enzymatic specificity. Focusing on the 3' end of the target nucleic also minimize problems arising from stable secondary structures in the target DNA. As shown in FIG. 3B, ligation can be used to enhance the fidelity of detecting the 5'-terminal sequence of a target DNA.

EXAMPLE 4

Extension of Hybridized Probe Arrays With DNA Polymerase

Figure 4:
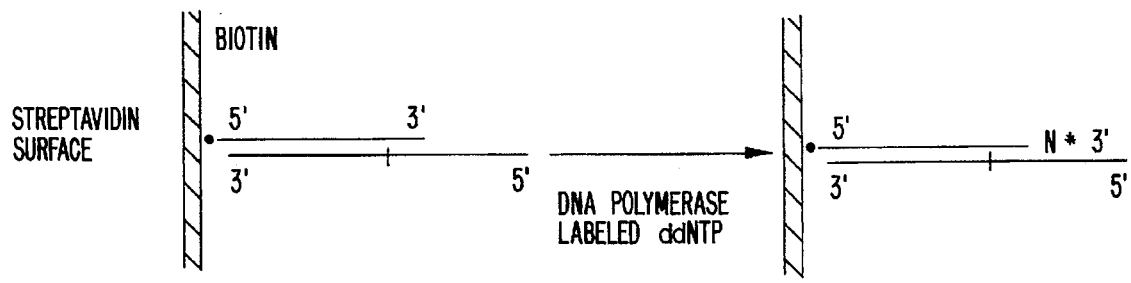
FIG. 4 Single nucleotide extension of a probe hybridized with a target nucleic acid using DNA polymerase and a single dideoxynucleotide.

Ligation ensures the fidelity of detection of the 3' terminal base of the target DNA. To ensure similar fidelity of detection at the 5' end of the duplex formed between the probe and the target, the probe-target duplex can be extended after ligation by one nucleotide using, for example, a labeled ddNTP (FIG. 4). This has two major advantages. First, specificity is increased because extension with the Klenow fragment of DNA polymerase requires a correctly base paired 3'-primer terminus. Second, using labeled ddNTPs one at a time, or a mixture of all four labeled with four different colors simultaneously, the identity of one additional nucleotide of the target nucleic acid can be determined as shown in FIG. 4. Thus, an array of only 1024 probes would actually have the sequencing power of an array of 4096 hexamers, in other words, a corresponding four-fold gain for any length used. In addition, polymerases work well in solid state sequencing methodologies quite analogous of the type proposed herein.

EXAMPLE 5

Positional Sequencing by Hybridization With a Nested Set of DNA Samples

Figure 5:
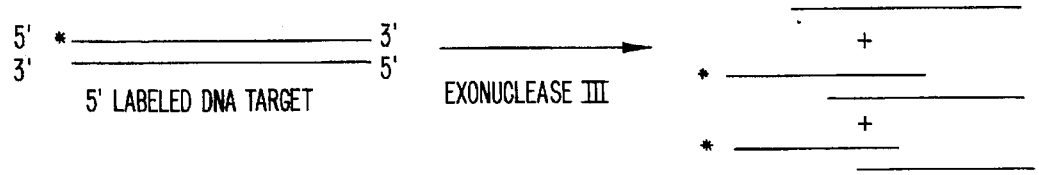
FIG. 5 Preparation of a nested set of targets using labeled target nucleic acids partially digested with Exonudease III.

Thus far described arrays have been very inefficiently utilized because with only a single target nucleic acid, only a single probe will be detected. This clearly wastes most of the potential information intrinsically available from the array. A variation in the procedures will use the array much more efficiently. This is illustrated in FIG. 5. Here, before hybridization to the probe array, the 5'-labeled (or unlabeled) target nucleic acid is partially degraded with an enzyme such as exonuclease III. Digestion produces a large number of molecules with a range of chain lengths that share a common 5'-terminus, but have a variable 3'-terminus. This entire family of nucleic acids is then hybridized to the probe array. Assuming that the distribution of 3'-ends is sufficiently broad, the hybridization pattern should allow the sequence of the entire target to be read subject to any branch point ambiguities. If a single set of exonuclease conditions fails to provide a broad enough distribution, samples could be combined and prepared under several different conditions.

In addition, there are alternative methods of preparing the desired samples, such as polymerization in the absence of limiting amounts of one of the substrate bases, such as for DNA, one of the four dNTPs. Standard Sanger or Maxam-Gilbert sequencing protocols cannot be used to generate the ladder of DNA fragments because these techniques fail to yield 3'-ligatable ends. In contrast, sequencing by the method of the present invention combines the techniques and advantages of the power of ladder sequencing with the parallel processing power of positional sequencing by hybridization.

EXAMPLE 6

Retaining Positional Information in Sequencing by Hybridization

Inherent in the detection of just the 3'-terminal sequence of the target nucleic acid, is the possibility of obtaining information about the distance between the sequence hybridized and a known reference point. Although that point could be arbitrary, the 5'-end of the intact target was used. The desired distance is then just the length of the DNA fragment that has hybridized to a particular probe in the array. In principle, there are two ways to determine this length. One is to length fractionate (5' labeled) DNA before or after the hybridization, ligation, and any DNA polymerase extension. Single DNA sequences could be used, but pools of many DNA targets used simultaneously or, alternatively, a double labeled target with one color representing the 5'-end of any unique site, would be more efficient. For example, incorporated into the target is a fractional amount, for example, about 1%, of biotinylated (or digoxigenin-labeled) pyrimidines, and use this later on for fluorescent detection. The ratio of the internal label to the end label is proportional to target fragment length. For any particular sample the relationship is monotonic even though it may be irregular. Thus, correct order is always obtained even if distances are occasionally distorted by extreme runs of purines of pyrimidines. If necessary, it is also possible to use two quasi-independent internal labeling schemes.

The scheme as just outlined, used with polymerase extension, might require as many as 6 different colored labels; 2 on the target (5' and internal) and four on the probe extension (four ddNTPs). However the 5' label is unnecessary, since the 3' extension provides the same information (providing that the DNA polymerase reaction is dose to stoichiometric). The ddNTPs can be used one at a time if necessary. Therefore, the scheme could proceed with as little as two color detection, if necessary (FIG. 6), and three colors would certainly suffice.

Figure 6:
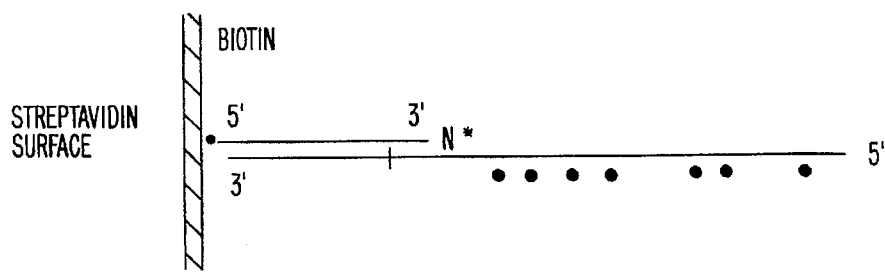
FIG. 6 Determination of positional information using the ratio of internal label to terminal label.

A scheme complementary to that shown in FIG. 6 would retain positional information while reading the 5'-terminal sequence of 3'-end labeled plus internally labeled target nucleic acids. Here, as in FIG. 3B, probe arrays with 5' overhangs are used, however, polymerase extension will not be possible.

EXAMPLE 7

Resolution of Branch Point Ambiguities

Branch point ambiguities are caused by sequence recurrence and effectively limit the size of the target nucleic acid to a few hundred base pairs. However, positional information derived from Example 6 will resolve almost all of these ambiguities. If a sequence recurs, more than one target fragment will hybridize to, or otherwise be detected by subsequent ligation to or extension from a single immobilized probe. The apparent position of the target will be its average on the recurrent sequence. For a sequence which occurs just twice, the true location is symmetric around the apparent one. For example, the apparent position of a recurrent sequence occurring in positions 50 and 100 bases from the 5'-end of the target will be 75 bases from the end. However, when the pattern of positional sequencing by hybridization is examined, a sequence putatively located at that position will show overlap with contacts in the neighborhood of 50 bases and 100 bases from the 5'-end. This will indicate that a repeat has occurred.

Additional information is available for the recurrence of pentanucleotide sequences by the use of polymerase and single base extension as described in Example 4. In three cases out of four the single additional base will be different for the two recurrent sequences. Thus, it will be clear that a recurrence has occurred.

The real power of the positional information comes, not from its application to the recurrent sequences, but to its applications to surrounding unique sequences. Their order will be determined unequivocally, assuming even moderately accurate position information, and thus, the effect of the branch point will be eliminated. For example, 10% accuracy in intensity rations for a dual labeled 200 base pair target will provide a positional accuracy of 20 base pair. This would presumably be sufficient to resolve all but the most extraordinary recurrences.

EXAMPLE 8

Extending the 3'-sequence of the Target

Figure 7A:
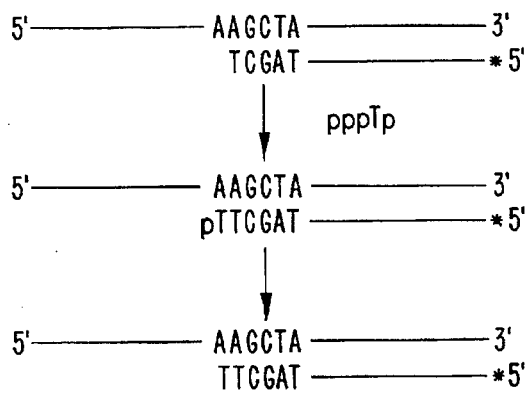
FIG. 7 (A) Extension of one strand of the probe using hybridized target as template with a single deoxynucleotide. (B) Hybridization of target with a fixed probe followed by ligation of probe to target.
Figure 7B:
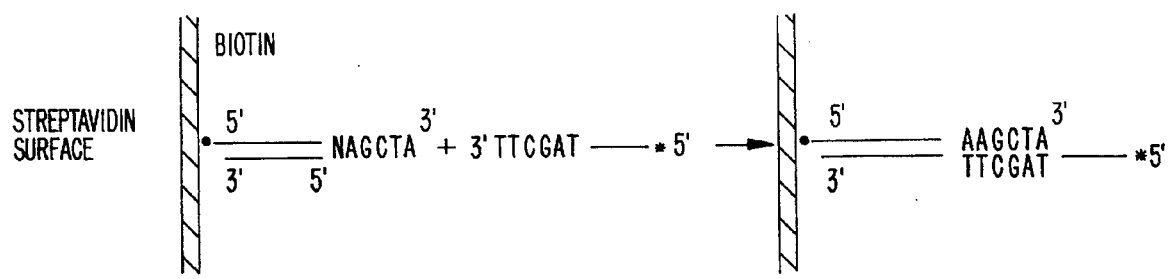

Using the scheme shown in FIGS. 7A and 7B, it is possible to learn the identity of the base 3' to the known sequence of the target, as revealed by its hybridization position on an oligonucleotide array. For example, an array of $4^n$ single stranded overhangs of the type NAGCTA 3', as shown in the Figure, are created wherein n is the number of known bases in an overhang of length n+1. The target is prepared by using a 5' label in the manner shown in FIG. 5. The Klenow fragment of DNA polymerase would then be used to acid a single dpppNp as a polymerization chain terminator. Before hybridization the resulting 3'-terminal phosphate would be removed by alkaline phosphatase. This would allow subsequent ligation of the target to the probe array. Either by four successive single color 5' labels, or a mixture of four different colored chains, each color corresponding to a particular chain terminator, one would be able to infer the identity of the base that had paired with the N next to the sequence AGCTA. Labeling of the 5' end minimizes interference of fluorescent derivatives on the ligation step. Assuming that there are sufficient colors in a polychromatic detection scheme, this 3' target extension can be combined with the 3' probe extension to read n+2 bases in an array of complexity $4^n$. This is potentially quite a substantial improvement. It decreases the size of the array needed by a factor of 16 without any loss in sequencing power. However, the number of colors required begins to become somewhat daunting. In principle one would want at least nine, four for each 3' extension and one general internal label for target length. However, with resonance ionization spectroscopy (RIS) detection, eight colors are available with just a single type metal atom, and many more could be had with just two metals.

EXAMPLE 9

Extending the 5' Sequence of the Target

In example 4, it was illustrated that by polymerase extension of the 3'-end of the probe, a single additional nucleotide on the target could be determined after ligation. That procedure used only chain terminators. Florescent labeled dNTPs that serve as substrates for DNA polymerase and other enzymes of DNA metabolism can also be made. The probe-target complex of each ligation reaction with, for example, three labeled dNTPs and a fourth unlabeled chain terminator could be extended using fluorescent labeled dNTPs. This could be repeated, successively, with each possible chain terminator. If the ratio of the intensities of the different labels can be measured fairly accurately, a considerable amount of additional sequence information will be obtained. If the absolute intensities could be measured, the power of the method appears to be very substantial since one is in essence doing a bit of four color DNA sequencing at each site on the oligonucleotide array. For example, as shown in FIG. 8, for the sequence $(Pu)_4T$, such an approach would unambiguously reveal 12 out of the 16 possible sequences and the remainder would be divided into two ambiguous pairs each.

EXAMPLE 10

Sample Pooling in Positional Sequencing by Hybridization

A typical 200 base pair target will detect only 196 probes on a five base 1024 probe array. This is not far from the ideal case in single, monochromatic sampling where one might like to detect half the probes each time. However, as the procedure is not restricted to single colors, the array is not necessarily this small. With an octanucleotide array, in conventional positional sequencing by hybridization or one of its herein described enhancements, the target detects only $\frac{1}{32}$ of the immobilized probes. To increase efficiency a mixture of 16 targets can be used with two enhancements. First, intelligently constructed orthogonal pools of probes can be used for mapping by hybridization. Hybridization sequencing with these pools would be straightforward. Pools of targets, pools of probes, or pools of both can be used.

Second, in the analysis by conventional sequencing by hybridization of an array of $2 \times 10^4$ probes, divided into as few as 24 pools containing $8 \times 10^3$ probes each, there is a great deal of redundancy. Excluding branch points, 24 hybridizations could determine all the nucleic acid sequences of all the targets. However, using RIS detection there are much more than 24 colors. Therefore, all the hybridizations plus appropriate controls could be done simultaneously, provided that the density of the nucleic acid sample were high enough to keep target concentration far in excess of all the probes. A single hybridization experiment could produce $4 \times 10^6$ base pairs of sequence information. An efficient laboratory could perform 25 such hybridizations in a day, resulting in a throughput of $10^8$ base-pairs of sequence per day. This is comparable to the speed of polymerization by *E. coli* DNA polymerase.

EXAMPLE 11

Oligonucleotide Ligation After Target Hybridization

Figure 9:
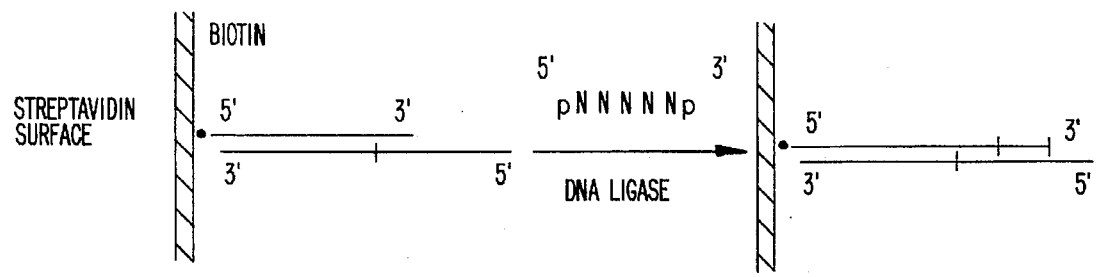
FIG. 9 Extension of a nucleic acid probe by ligation of a pentanucleotide 3' blocked to prevent polymerization.

Stacking hybridization without ligation has been demonstrated in a simple format. Eight-mer oligonucleotides, were annealed to a target and then annealed to an adjacent 5-mer to extend the readable sequence from 8 to 13 bases. This is done with small pools of 5-mers specifically chosen to resolve ambiguities in sequence data that has already been determined by ordinary sequencing by hybridization using 8-mers alone. The method appears to work quite well, but it is cumbersome because a custom pool of 5-mers must be created to deal with each particular situation. In contrast, the approach taken herein (FIG. 9), after ligation of the target to the probe, is to ligate a mixtures of 5-mers arranged in polychromatically labeled orthogonal pools. For example, using 5-mers of the form pATGCAp or pATGCddA, only a single ligation event will occur with each probe-target complex. These would be 3' labeled to avoid interference with the ligase. Only ten pools are required for a binary sieve analysis of 5-mers. In reality it would make sense to use many more, say 16, to introduce redundancy. If only four colors are available, those would require four successive hybridizations. For example, sixteen colors would allow a single hybridization. But the result of this scheme is that one reads ten bases per site in the array, equivalent to the use of $4^{10}$ probes, but one only has to make $2 \times 4^5$ probes. The gain in efficiency in this scheme is a factor of 500 over conventional sequencing by hybridization.

EXAMPLE 12

Synthesis of Custom Arrays of Probes

Figure 10:
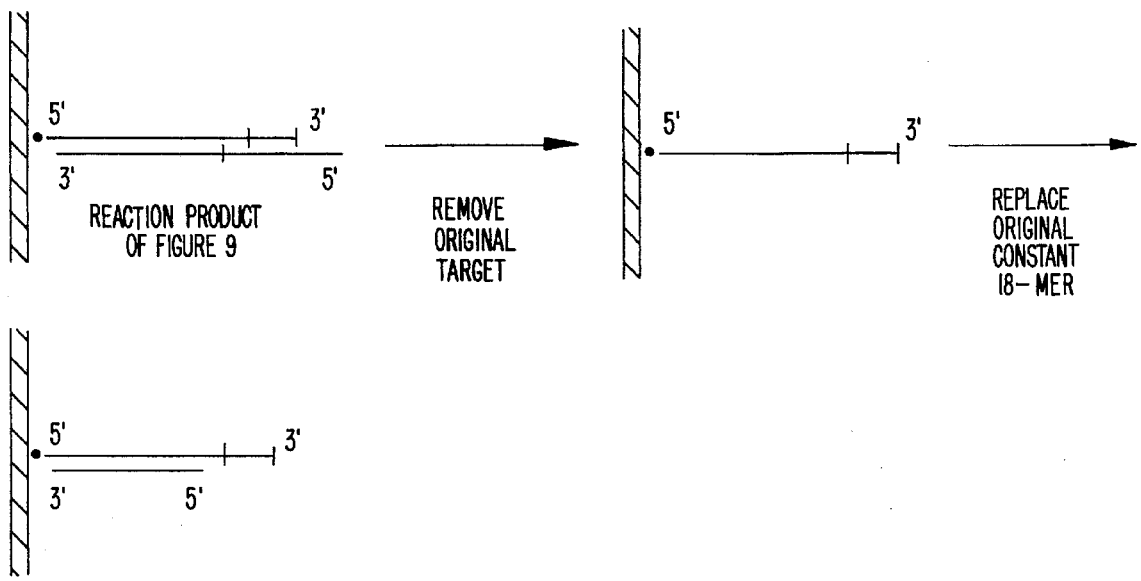
FIG. 10 Preparation of a customized probe containing a 10 base pair sequence that was present in the original target nucleic acid.

Custom arrays of probe would be useful to detect a change in nucleic acid sequence, such as any single base change in a preselected large population of sequences. This is important for detecting mutations, for comparative sequencing, and for finding new, potentially rare polymorphisms. One set of target sequences can be customized to an initial general array of nucleic acid probes to turn the probe into a specific detector for any alterations of a particular sequence or series of sequences. The initial experiment is the same as outlined above in Example 3, except that the 3'-blocked 5-mers are unlabeled. After the ligation, the initial nucleic acid target strand along with its attached 18 nucleotide stalk is removed, and a new unligated 18 nucleotide stalk annealed to each element of the immobilized array (FIG. 10). The difference is that because of its history, many (ideally 50% or more), of the elements of that array now have 10 base 3' extensions instead of 5 base extensions. These do not represent all $4^{10}$ possible 10-mers, but instead represent just those 10-mers which were present in the original sample. A comparison sample can now be hybridized to the new array under conditions that detect single mismatches in a decanucleotide duplex. Any samples which fail to hybridize are suspects for altered bases.

A problem in large scale diagnostic DNA sequencing is handling large numbers of samples from patients. Using the approach just outlined, a third or a fourth cycle of oligonucleotide ligation could be accomplished creating an array of 20-mers specific for the target sample. Such arrays would be capable of picking up unique segments of genomic DNA in a sequence specific fashion and detecting any differences in them in sample comparisons. Each array could be custom designed for one individual, without any DNA sequence determination and without any new oligonucleotide synthesis. Any subsequent changes in that individual's DNA such as caused by oncogenesis or environmental insult, might be easily detectable.

EXAMPLE 13

Positional Sequencing by Hybridization

Figure 12A:
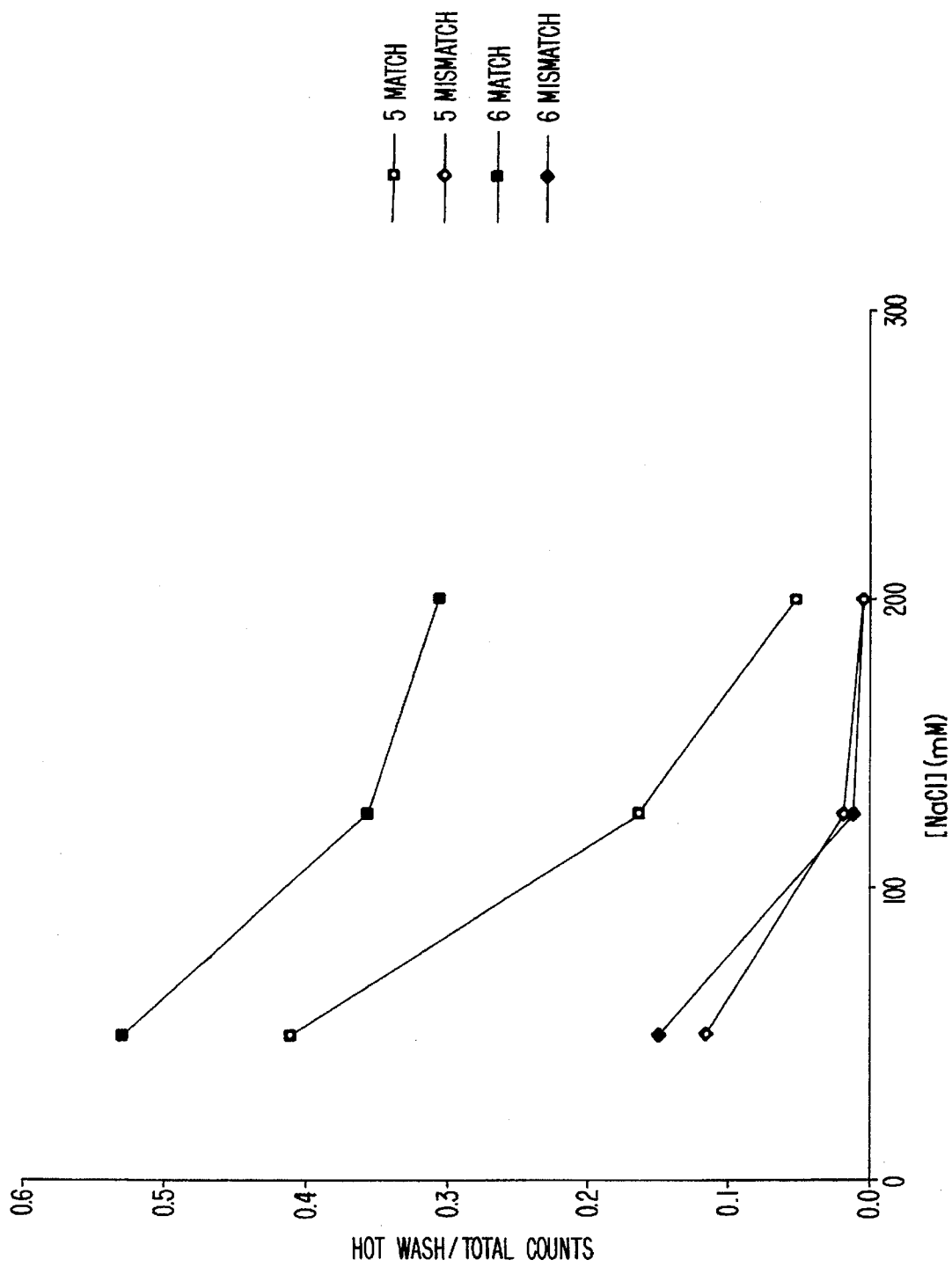
FIG. 12 (A) Graphical representation of the ligation efficiency of positional sequencing. Depicted is the relationship between the amount of label remaining over the total amounts of label in the reaction, verses NaCl concentration. (B) Test sequences of biotinylated duplex probes tethered to strepavidin coated magnetic microbeads utilized to determine ligation efficiency.

Hybridization was performed using probes with five and six base pair overhangs, including a five base pair match, a five base pair mismatch, a six base pair match, and a six base pair mismatch (FIGS. 12A and 12B). The biotinylated double stranded probe was prepared in TE buffer by annealing the complementary single strands together at 68° C. for five minutes followed by slow cooling to room temperature. A five-fold excess of monodisperse, polystyrene-coated magnetic beads (Dynal) coated with strepavidin was added to the double stranded probe, which as then incubated with agitation at room temperature for 30 minutes. After ligation, the samples were subjected to two cold (4° C.) washes followed by one hot (90° C.) wash in TE buffer. The ratio of $^{32}P$ in the hot supernatant to the total amount of $^{32}P$ was determined. At high NaCl concentrations, mismatched target sequences were either not annealed or were removed in the cold washes. Under the same conditions, the matched target sequences were annealed and ligated to the probe. The final hot wash removed the non-biotinylated probe oligonucleotide. This oligonucleotide contained the labeled target if the target had been ligated to the probe.

EXAMPLE 14

Data Processing and Interpretation

Highly automated methods for raw data handling and the generation of contiguous sequence information from hybridization result can be carried out. Several major efforts at software development for reading sequencing chip data and assembling it into a contiguous sequence are already underway. Such software is generally available in the interested user community. The most useful examples of this software can be customized to fit the particularly special needs of this approach including polychromatic detection, incorporation of positional information, and pooling schemes. Specific software developments for constructing and decoding the orthogonal pools of samples that may ultimately be used are being developed because these procedures are also needed for enhanced physical mapping methods.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

I claim:

1. A method for creating a nucleic acid probe array comprising the steps of:
   a) hybridizing a plurality of single-stranded first nucleic acids to a plurality of longer, single-stranded second nucleic acids complementary to the first nucleic acids wherein each second nucleic acid contains a variable terminal nucleotide sequence to form probes each having a double-stranded portion and a single-stranded portion with the variable nucleotide sequence in the single-stranded portion;
   b) hybridizing target nucleic acids to the probes;
   c) ligating hybridized targets to the first nucleic acids of the probes;
   d) isolating the second nucleic acids; and
   e) hybridizing additional first nucleic acids to isolated second nucleic acids to form the nucleic acid probe array.

2. The method of claim 1 wherein each first nucleic acid is about 15 to about 25 nucleotides in length and each second nucleic acid is about 20 to about 30 nucleotides in length.

3. The method of claim 1 wherein the double-stranded portion contains an enzyme recognition site.

4. The method of claim 1 further comprising the steps of hybridizing ligated probes with an array of oligonucleotides containing variable nucleotide sequences and ligating hybridized oligonucleotides to the second nucleic acids of the probes.

5. The method of claim 1 further comprising the step of enzymatically extending the second nucleic acids after hybridization with targets using the targets as a template.

6. The method of claim 1 further comprising a step of fixing any of said nucleic acids to a solid support.

7. The method of claim 6 wherein the solid support is a plastic, a ceramic, a metal, a resin, a gel, or a membrane.

8. A method for creating a nucleic acid probe array comprising the steps of:
   a) hybridizing a plurality of single-stranded first nucleic acids to a plurality of longer, single-stranded second nucleic acids complementary to the first nucleic acids wherein each second nucleic acid contains a variable terminal nucleotide sequence to form probes each having a double-stranded portion and a single-stranded portion with the variable nucleotide sequence in the single-stranded portion;
   b) hybridizing target nucleic acids to the probes;
   c) ligating hybridized targets to the first nucleic acids of the probes;
   d) hybridizing ligated probes to an array of oligonucleotides that contain variable nucleotide sequences;
   e) ligating hybridized oligonucleotides to the second nucleic acids of the probes;
   f) isolating ligated second nucleic acids; and
   g) hybridizing additional first nucleic acids to isolated second nucleic acids to form the nucleic acid probe array.

9. The method of claim 8 wherein each first nucleic acid is about 15 to about 25 nucleotides in length and each second nucleic acid is about 20 to about 30 nucleotides in length.

10. The method of claim 8 wherein the double-stranded portion contains an enzyme recognition site.

11. The method of claim 8 wherein the oligonucleotides are each about 4 to about 20 nucleotides in length.

12. The method of claim 8 which further comprising a step of fixing any of said nucleic acids to a solid support.

13. The method of claim 12 wherein the solid support is a plastic, ceramic, a metal, a resin, a gel, or a membrane.

14. A method for creating a nucleic acid probe array comprising the steps of:
   a) hybridizing a plurality of single-stranded first nucleic acids to a plurality of longer, single-stranded second nucleic acids complementary to the first nucleic acids wherein each second nucleic acid contains a variable terminal nucleotide sequence to form probes having a double-stranded portion and a single-stranded portion with the variable nucleotide sequence in the single-stranded portion;
   b) hybridizing target nucleic acids to the probes;
   c) ligating hybridized targets to the first nucleic acids of the probes;
   d) enzymatically extending each second nucleic acid using the target as a template;
   e) isolating extended second nucleic acids; and
   f) hybridizing additional first nucleic acids to isolated second nucleic acids to form the nucleic acid probe array.

15. The method of claim 14 wherein each first nucleic acid is about 15 to about 25 nucleotides in length and each second nucleic acid is about 20 to about 30 nucleotides in length.

16. The method of claim 14 wherein the double-stranded portion contains an enzyme recognition site.

17. The method of claim 10 further comprising a step of fixing any of said nucleic acids to a solid support.

18. The method of claim 17 wherein the solid support is a plastic, ceramic, a metal, a resin, a gel, or a membrane.

* * * * *

UNITED STATES PATENT AND TRADEMARK OFFICE
Certificate

Patent No. 5,631,134

Patented: May 20, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Charles R. Cantor, Boston, MA; Cassandra Smith, Boston, MA; and Takeshi Sano, Boston, MA.

Signed and Sealed this Twenty-eighth Day of December 2004.

W. GARY JONES
*Supervisory Patent Examiner*
Art Unit 1634

UNITED STATES PATENT AND TRADEMARK OFFICE
CERTIFICATE OF CORRECTION

PATENT NO.    : 5,631,134
DATED         : May 20, 1997
INVENTOR(S)   : Charles R. Cantor It is certified that error appears in the above-identified patent and that said Letters Patent is hereby corrected as shown below:

Title page, Item [54] and Column 1, line 2,
Title, the word "HYBRIDATION" should read -- HYBRIDIZATION --.

Signed and Sealed this

First Day of February, 2005

JON W. DUDAS
*Director of the United States Patent and Trademark Office*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TCGAGAACCT TGGCT 15

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTGATGCGTC GGATCATC 18

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATGATCCGA CGCATCAGAG CTC 23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GATGATCCGA CGCATCAGAG CTT 23

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GATGATCCGA CGCATCAGAG CTCT                                                                                   24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATGATCCGA CGCATCAGAG TTCT                                                                                   24